US00PP32442P2

(12) United States Plant Patent
Lenard-Fountain

(10) Patent No.: US PP32,442 P2
(45) Date of Patent: Nov. 10, 2020

(54) ***DIGITALIS* PLANT NAMED 'ISOB007'**

(50) Latin Name: *Digitalis isabelliana*
Varietal Denomination: ISOB007

(71) Applicant: Birdie Lenard-Fountain, Valley Center, CA (US)

(72) Inventor: Birdie Lenard-Fountain, Valley Center, CA (US)

( * ) Notice: Subject to any disclaimer, the term of this patent is extended or adjusted under 35 U.S.C. 154(b) by 0 days.

(21) Appl. No.: 16/602,987

(22) Filed: Jan. 10, 2020

(30) Foreign Application Priority Data

May 14, 2019 (QZ) ..... PBR 20191211

(51) Int. Cl.
*A01H 5/02* (2018.01)
*A01H 6/68* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Digitalis* plant named 'ISOB007' that is characterized by its compact and well-branched plant habit, its freely flowering habit, and its flowers that are apricot orange in color.

2 Drawing Sheets

Botanical classification: *Digitalis isabelliana.*
Cultivar designation: 'ISOB007'.

CROSS-REFERENCE TO A RELATED APPLICATION

This application claims priority to European Community Plant Variety Office (CPVO) Plant Breeder's Rights Application No. 2019/1211 filed on May 14th 9, 2019, under 35 U.S.C. 119(f), the entire contents of which is incorporated by reference herein.

BACKGROUND OF THE INVENTION

The present invention relates to a new and distinct cultivar of *Digitalis isabelliana* and will be referred to hereafter by its cultivar name, 'ISOB007'. 'ISOB007' represents a new cultivar of Canary Island foxglove; an herbaceous perennial grown for landscape use.

'ISOB007' was discovered by the Inventor as a branch mutation of an unnamed and unpatented plant of *Digitalis isabelliana* that was growing in a container in Valley Center, Calif. in June of 2010.

Asexual propagation of the new cultivar was first accomplished by stem cuttings under the direction of the Inventor in July of 2010 in Bonsall, Calif. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'ISOB007' as a unique cultivar of *Digitalis.*

1. 'ISOB007' exhibits a compact and well-branched plant habit.
2. 'ISOB007' exhibits a freely flowering habit.

3. 'ISOB007' exhibits flowers that are apricot orange in color.

The parent plant of 'ISOB007' differs from 'ISOB007' in having a less compact plant habit, less branching, and in being less floriferous. There are no known cultivars in cultivation of the species *Digitalis isabelliana* known to the Inventor for comparison.

BRIEF DESCRIPTION OF THE DRAWINGS

The accompanying colored photographs illustrate the overall appearance and distinct characteristics of the new *Isoplexis*. The photographs were taken of a one-year-old plant of 'ISOB007' as grown outdoors in a 17-cm container in Boskoop, The Netherlands.

The photograph in FIG. 1 provides a side view of a plant of 'ISOB007' in bloom.

Figure 1:
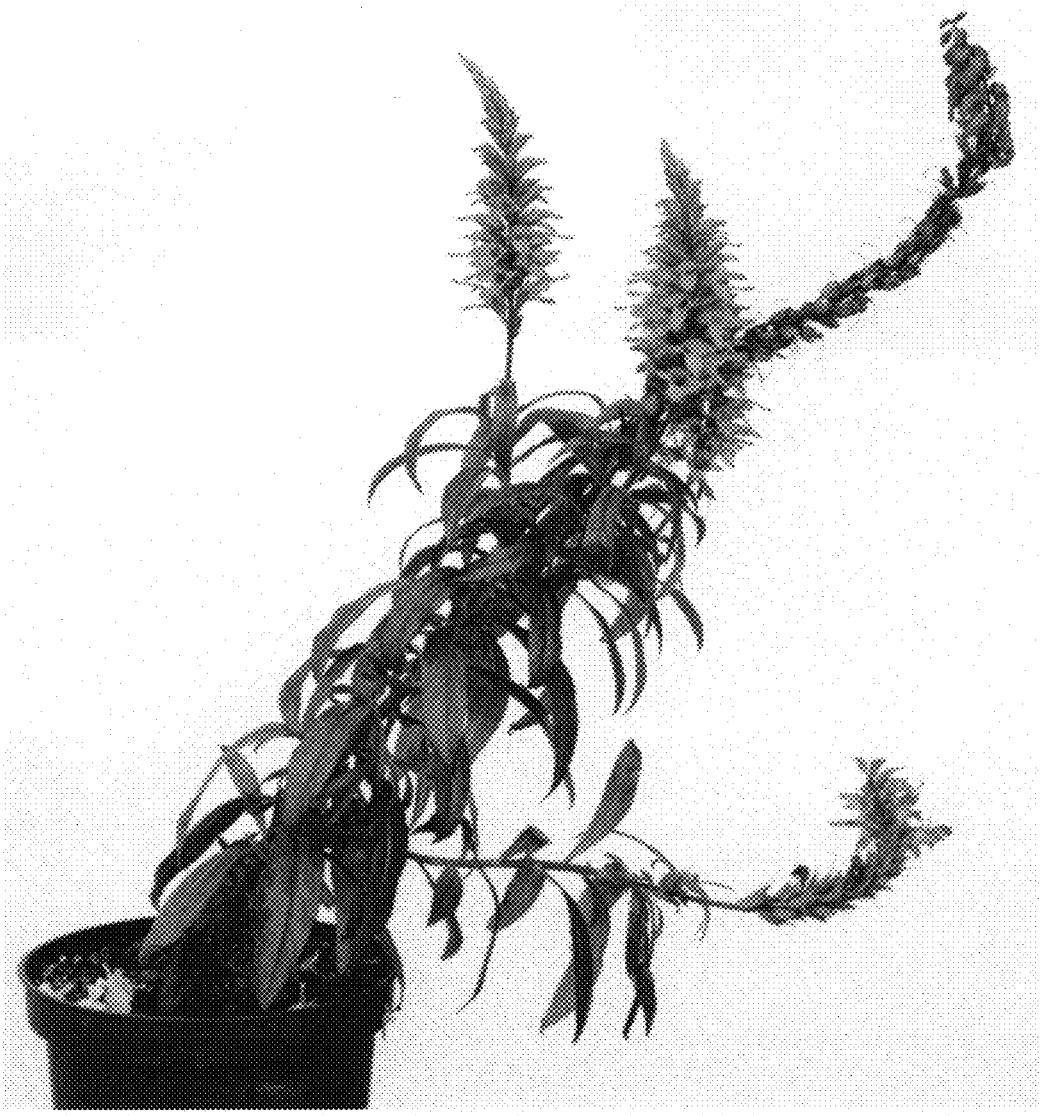
Figure 2:
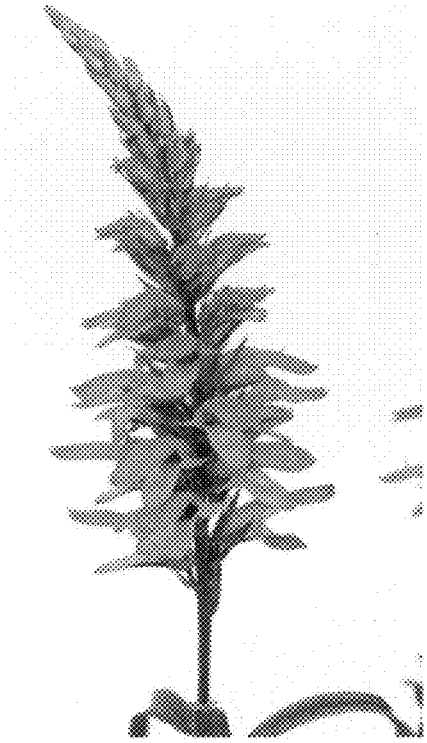

The photograph in FIG. 2 provides a close-up view of an inflorescence of 'ISOB007'.

Figure 3:
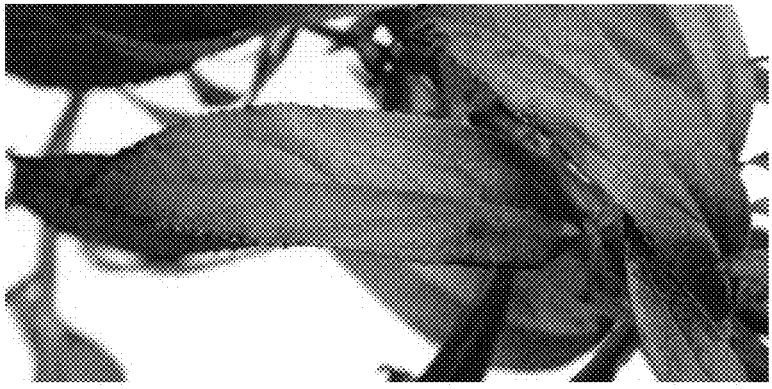

The photograph in FIG. 3 provides a close-up view of the foliage of 'ISOB007'.

The colors in the photograph may differ slightly from the color values cited in the detailed botanical description, which accurately describe the colors of the new *Digitalis.*

DETAILED BOTANICAL DESCRIPTION

The following is a detailed description of the new cultivar as observed for plants about one year in age as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Summer into autumn in The Netherlands.

*Plant type*.—Herbaceous perennial.

*Plant habit*.—Upright and compact.

*Height and spread*.—Average of 35.4 cm in height from soil to top of foliar plane, 60.5 cm in height from soil level to top of floral plane, 30.3 cm in diameter as grown in the landscape.

*Hardiness*.—At least in U.S.D.A. Zones 7 to 11.

*Diseases and pests*.—No susceptibility or resistance to diseases or pests has been observed.

*Propagation*.—Stem cuttings.

*Root development*.—About 7 days to initiate roots and 4 to 5 weeks to produce a young rooted plant.

*Growth rate*.—Moderate.

Stem description:

*Shape*.—Round.

*Stem quantity*.—Well-branched with an average of 1 main branch and 5 lateral branches per main branch.

*Stem color*.—Young stems; 146B, tinged N187B, mature stems and internodes; a color between 200A and N187A.

*Stem size*.—Average of 4 mm in diameter and 10.5 cm (excluding inflorescence) in length.

*Stem surface*.—Slightly glossy and densely covered with soft pubescence hairs; an average of 0.4 mm in length and 157D in color.

*Stem strength*.—Moderately strong.

*Stem aspect*.—Main branches held at an average angle of 40° to vertical, lateral branches held at an average angle of 45° to main branches.

*Internode length*.—Average of 7 mm.

Foliage description:

*Leaf division*.—Simple.

*Leaf arrangement*.—Alternate.

*Leaf shape*.—Narrow elliptic and moderately curved downward.

*Leaf size*.—An average of 11.4 cm in length and 2.5 cm in length.

*Leaf number*.—Average of 15 per lateral branch.

*Leaf base*.—Cuneate.

*Leaf apex*.—Acute.

*Leaf margin*.—Serrate.

*Leaf venation*.—Pinnate, upper surface 200D in color, lower surface 146 in color.

*Leaf surface*.—Both surfaces smooth, moderately leathery and glabrous except for very short pubescent hairs covering the margins; average of 0.75 mm in length and 157D in color.

*Leaf color*.—Young upper surface; NN137B, young lower surface; 146A, mature upper surface; 147A, mature lower surface; 147B.

Flower description:

*Inflorescence type*.—Terminal racemes.

*Lastingness of inflorescence*.—Individual flowers last an average of 14 days, self-cleaning.

*Inflorescence size*.—Terminal; average of 28.5 cm in height, 6.1 cm in diameter, secondary average of 14.6 cm in height, 6.1 cm in diameter.

*Flower type*.—Single, zygomorphic.

*Flower number*.—50 to 100 per inflorescence, 300 per plant.

*Flower aspect*.—Outward.

*Flower fragrance*.—None.

*Flower buds*.—Ovate in shape, average of 9 mm in length and 4 mm in diameter, color; 144C, lower side 144D, immature calyx N170B, surface is smooth, glabrous and matte.

*Flower size*.—Average of 2.3 cm in height, 2.6 cm in diameter, 3 cm in depth, throat; average of 9 mm in length, 4 mm in diameter, tube; average of 9 mm in length, is 1 cm in diameter and 5 mm at base.

*Flower shape*.—Zygomorphic.

*Peduncle*.—Held in a vertical angle, moderately strong, surface is smooth, glabrous, matte, 183C in color, terminal size; average of 25.7 cm in length, 2 mm in width, lateral size; average of 11.8 cm in length, 2 mm in diameter.

*Pedicels*.—Average of 3.5 mm in length and 0.5 mm in width, held at an average angle of 40°, strong, surface is smooth, glabrous and matte, 178B in color.

*Calyx*.—Rotate in shape, tubular, average of 7 mm in length and 1.2 cm in diameter.

*Sepals*.—5, rotate, 1 whorl, obovate in shape, 27.5% of base is fused, narrow acuminate apex, entire margins, both surfaces smooth, glabrous and matte, color; when opening upper surface 144D, when opening lower surface 144C, when fully open upper and lower surface 143B, changing to 146A at the top.

*Petals*.—5, (1 lower petal, 2 lateral petals, 2 fused upper petals), 1 whorl, narrowly ovate to slightly curved backwards, acute apex, 9 mm of base is fused, lobes; entire margins, upper petals glabrous and smooth, lower and lateral petals matte and densely covered with very short glandular hairs; average of 0.2 mm and matches surface color, lower and lateral petals; average of 2 cm in length, 3.5 mm to 7 mm in width, upper petals (fused); average of 2.8 cm in length, 1 cm in width, color: when opening upper surface; lower and lateral petals N170C, tinged 145C with tip 172B and 173A, upper petals 145C, tip margined 171D, when opening lower surface; lower and lateral petals 166B, changing to 145C at the base, upper petals 164B, fading to 145C at the base, when fully open upper surface; lower and lateral petals 165B, fading towards the tube changing to 164B, upper petals 164C, fading towards the tube to 160D, tip of petals margined 171D, when fully open lower surface; lower and lateral petals 164B, margined 164A, upper petals N167B, changing towards the base to 164C and N167C, veins on upper petals 164A, throat color; 161A, tube color; inner surface 160D, outer surface 164B.

Reproductive organs:

*Gynoecium*.—Pistil; 1, 2.1 mm in length, style; 2 cm in length, 183C in color, stigma; pointed, 148D in color, ovary; 143A to 143B in color.

*Androecium*.—Stamens; 4, filament; 1.8 cm in length, 183D in color, anthers; basifixed, oblong in shape, 3 mm in length, 2 mm in width, 151D in color, pollen; high in quantity, 13D in color.

*Fruit and seed*.—Fruit and seed production have not been observed to date.

It is claimed:

1. A new and distinct cultivar of *Digitalis* plant named 'ISOB007' as herein illustrated and described.

* * * * *